(12) United States Patent
Schenk

(10) Patent No.: US 8,426,197 B2
(45) Date of Patent: *Apr. 23, 2013

(54) METHODS AND APPARATUS FOR REDUCING PROTEIN CONTENT IN SPERM CELL EXTENDERS

(75) Inventor: John L. Schenk, Fort Collins, CO (US)

(73) Assignee: XY, LLC, Navasota, TX (US)

( * ) Notice: Subject to any disclaimer, the term of this patent is extended or adjusted under 35 U.S.C. 154(b) by 679 days.

This patent is subject to a terminal disclaimer.

(21) Appl. No.: 12/619,586

(22) Filed: Nov. 16, 2009

(65) Prior Publication Data

US 2010/0216111 A1    Aug. 26, 2010

Related U.S. Application Data

(63) Continuation of application No. 11/219,607, filed on Sep. 2, 2005, now Pat. No. 7,618,770.

(60) Provisional application No. 60/704,001, filed on Jul. 29, 2005.

(51) Int. Cl.
    *A01N 1/02* (2006.01)

(52) U.S. Cl.
    USPC .............................. 435/325; 435/2; 424/93.7

(58) Field of Classification Search .............. 435/2, 325, 435/93.7; 424/93.7
    See application file for complete search history.

(56) References Cited

U.S. PATENT DOCUMENTS

| | | | |
|---|---|---|---|
| 4,007,087 A | 2/1977 | Ericsson | |
| 4,474,875 A | 10/1984 | Shrimpton | |
| 5,316,540 A | 5/1994 | McMannis et al. | |
| 7,105,355 B2 | 9/2006 | Kurabayashi et al. | |
| 7,618,770 B2 * | 11/2009 | Schenk | 435/2 |
| 2002/0131957 A1 | 9/2002 | Gavin et al. | |
| 2003/0157475 A1 | 8/2003 | Schenk | |
| 2007/0026378 A1 | 2/2007 | Schenk | |

FOREIGN PATENT DOCUMENTS

WO    2007016090 A2    2/2007

OTHER PUBLICATIONS

Abeydeera et al. Birth of Piglets Preselected for Gender Following In Vitro Fertilization on In Vitro Matured Pig Oocytes by X and Y Chromosome Dearing Spermatozoa Sorted by High Speed Flow Cytometry. Theriogenology 50: 981-988, 1998.
New Zealand Examination Report dated Apr. 18, 2011, issued in corresponding New Zealand Application No. 592269 (2 pages).
New Zealand Examination Report dated Apr. 18, 2011, issued in corresponding New Zealand Application No. 592268 (2 pages).
New Zealand Examination Report dated Apr. 18, 2011, issued in corresponding New Zealand Application No. 592267 (2 pages).
New Zealand Examination Report dated Apr. 18, 2011, issued in corresponding New Zealand Application No. 592266 (2 pages).
New Zealand Examination Report dated Apr. 18, 2011, issued in corresponding New Zealand Application No. 592270 (2 pages).
Australian Examiner's First Report dated May 18, 2011, issued in corresponding Australian Application No. 2006275984 (2 pages).
Parallel International patent application No. PCT/US06/28846; International Search Report dated Sep. 6, 2009.
Parallel International patent application No. PCT/US06/28846; Written Opinion of the International Searching Authority dated Sep. 6, 2009.
Parallel International patent application No. PCT/US06/28846; International Preliminary Report on Patentability dated Jan. 29, 2008.
U.S. Appl. No. 11/219,607, filed Sep. 2, 2005, to be issued Nov. 17, 2009 as patent No. 7618770.
Parallel New Zealand application No. 566129, First Examination Report dated, Feb. 12, 2010, 2 pages.
Japanese Notice of Reasons for Rejection dated Jan. 23, 2012, issued in corresponding JP Application No. 2008-524067 (4 pages).
European Extended Search Report dated Apr. 10, 2012, issued in corresponding EP Application No. 06800316.9 (7 pages).
Australian Examiner's Report No. 2 dated Apr. 16, 2012, issued in corresponding AU Application No. 2006275984 (3 pages).
McGonagle, Linda S. et al.; "The Influence of Cryoprotective Media and Processing Procedures on Motility and Migration of Frozen-Thawed Human Sperm"; Article, Jun. 30, 2002, pp. 137-141, vol. 4, No. 2, Asian Journal of Andrology (3 pages).
Robbins, R. K., et al.; "Influence of Freeze Rate, Thaw Rate and Glycerol Level on Acrosomal Retention and Survival of Bovine Spermatozoa Frozen in French Straws"; Article, Jan. 31, 1976, pp. 145-154, vol. 42, No. 1, Journal of Animal Science (12 pages).
Japanese Official Action dated Sep. 3, 2012 issued in corresponding Japan Application No. 2008-524067 (6 pages).
Chilean Office Action dated Nov. 19, 2009 issued in corresponding Chile Application No. 1986-06 (3 pages).

* cited by examiner

*Primary Examiner* — Ruth Davis
(74) *Attorney, Agent, or Firm* — Ryan Christensen; Cindee R. Ewell

(57) ABSTRACT

The inventive technology relates to methods and apparatus for reducing protein content in sperm cell extenders and may include one or more of the following features: techniques for reducing protein content in a sperm cell extender; techniques for reducing protein content in a cryoprotectant-containing B fraction of a sperm cell extender; techniques for preparing sperm cell extenders that do not require clarification; techniques for preparing low density gradient sperm cell extenders suitable for centrifugation; techniques for reducing protein content between individual steps in preparing a sperm cell extender, and techniques for establishing novel values of reduced protein content in sperm cell extenders.

27 Claims, 5 Drawing Sheets

METHODS AND APPARATUS FOR REDUCING PROTEIN CONTENT IN SPERM CELL EXTENDERS

This application is a continuation of, and claims priority, to U.S. patent application Ser. No. 11/219,607 filed Sep. 2, 2005, issued as U.S. Pat. No. 7,618,770 which claims the benefit of U.S. Provisional Application No. 60/704,001, filed Jul. 29, 2005, both of which are hereby incorporated herein by reference.

BACKGROUND OF THE INVENTION

Generally, the inventive technology disclosed herein relates to methods and apparatus for reducing protein content in sperm cell extenders. More specifically, this inventive technology may involve eliminating the protein content of a cryoprotectant component used in a multiple step sperm cell extension process. The inventive technology may be particularly suited for use in sorted sperm applications.

Sperm cell extenders may be commonly used in a variety of biological disciplines that require working with sperm cells. For example, one discipline that may make extensive use of sperm cell extenders is the field of artificial insemination. Whereas natural insemination may involve direct male to female insemination, artificial insemination may typically involve collecting sperm cells from a male, performing a degree of human manipulation of such sperm cells removed from their natural environment, and then inserting the manipulated sperm cells into a female. The precise degree of human manipulation may vary depending on the precise nature of the particular application. For example, some human manipulation may simply involve dividing a collected sperm sample into multiple doses for use in multiple insemination events, possibly with multiple female animals. However, other applications may require more intensive human manipulation.

For example, human manipulation in some applications may involve sorting sperm cells into populations based on characteristics exhibited by sperm cells. One such application may include the use of flow cytometry to separate sperm cells into populations of X-chromosome-bearing and Y-chromosome bearing sperm cells. A flow cytometer may typically accomplish such separation by flowing sperm cells entrained in a fluid stream one at a time through an interrogation region, where information about each sperm cell may be obtained. Interrogation may typically be accomplished through the use of optics, for example perhaps by intersecting a laser beam with a sperm cell and measuring the resulting light scatter or fluorescence. The determination of a sex characteristic perhaps may be made by staining the sperm cells with a fluorescent dye that binds to the DNA within individual sperm cells. When a laser illuminates individual sperm cells, the dye may fluoresce. Sorting of sperm cells according to a sex characteristic may then be accomplished, perhaps by recognizing that sperm cells bearing an X chromosome have more DNA than sperm cells bearing a Y chromosome, thus possibly emitting more fluorescent light when excited by a laser and perhaps allowing the cell to be identified and separated.

Another example of human manipulation may involve perhaps freezing sperm cells for use at a later time. Freezing sperm cells may often be critical to the effective use of sperm cells, because freezing may preserve at least some degree of the viability of sperm cells for a period of time extended beyond a point at which such viability otherwise may typically become compromised. Such extension of sperm cell viability may be accomplished in freezing techniques perhaps by slowing the metabolism of sperm cells and perhaps extending their useful life accordingly. In particular, it perhaps may be known that sperm cell metabolism may be slowed by about 50% approximately for every 10 degrees Celsius to which a sperm cell is cooled. Moreover, frozen sperm cells may be packaged in formats convenient for particular applications, for example perhaps as frozen straws, frozen pellets, or other forms of frozen artificial samples. Frozen sperm cells also may lend themselves well to transportation over large distances, for example as where a sperm cell collection facility, sperm cell extension facility, and artificial insemination facility may be widely dispersed at different locations.

It may be appreciated that the removal of sperm from their natural environment may remove them from natural support mechanisms that maintain their viability. Sperm cell extenders may act to restore at least a degree of such support to sperm cells. For example, one function of sperm cell extenders may be to buffer sperm cells, for example perhaps by adjusting the pH or osmoality of a medium into which sperm cells may be placed. Another function of sperm cells extenders perhaps may be to provide nutrients to sperm cells or to serve as a sperm cell energy source. In freezing applications, a further function may be to serve as a cryoprotectant to minimize the adverse effects of freezing upon sperm cells. It may be appreciated that such functions of sperm cell extenders may be accomplished at least to some degree by the constituent parts that make up any individual sperm cell extender.

For example, protein content may be a frequently used constituent part of various types of sperm cells extenders. Protein content may serve one or more functions in a sperm cell extender. A primary purpose of protein content may be to provide nutrients and perhaps serve as an energy source for sperm cells. However, some kinds of protein may also have a cryoprotectant function, for example, perhaps the use of lipoproteins to replace lipids lost from sperm cell membranes that may be due to a freezing process. Moreover, protein content in sperm cell extenders may take a variety of forms. Some protein content may be plant-based, for example lecithin derived from soy. Other protein content may be animal-based, for example, perhaps egg yolk derived from sources including common hen's eggs.

Cryoprotectants also may be an example of a frequently used constituent part of various types of sperm cell extenders. Moreover, cryoprotectants may take a variety of forms in sperm cell extenders. One commonly used cryoprotectant may be glycerol. Glycerol may protect sperm cells during a freezing process, perhaps by binding to water contained within and surrounding a sperm cell, perhaps dehydrating the sperm cell as a result, and accordingly perhaps reducing the formation of intracellular ice that may cause damage to the sperm cell. However, using glycerol to cryoprotect sperm cells also may entail certain disadvantages. For example, glycerol may pose at least a degree of toxicity to sperm cells, the effect of which may become more pronounced with larger amounts of glycerol. Further, glycerol may be hyperosmotic to sperm cells, which may result in a degree of shock to sperm cells to which glycerol has been added. In particular, such hyperosmotic properties of glycerol may cause a sperm cell coming into contact with glycerol to rapidly shrink or expand as a result of a difference in solute concentration across the sperm cell's membrane. Such rapid shrinking and expanding may perhaps cause damage to a sperm cell.

Accordingly, certain procedures may have been developed for sperm cell extenders to minimize the adverse effects of glycerol on sperm cells. For example, as a practical matter it may perhaps be recognized that combining glycerol with sperm cells at reduced temperatures may reduce the toxic effects of glycerol on sperm cells. Accordingly, sperm cell extenders using glycerol often may be prepared in a multiple step process involving two or more extender fractions. More particularly, certain sperm cell extenders may contain an "A" fraction without glycerol and a "B" fraction with glycerol. This may allow a sperm cell extender to be prepared in two or more steps, for example, a first step in which sperm cells may be added to the A fraction of a sperm cell extender at perhaps room temperature, followed by a second step in which the sperm cells added to the A fraction are cooled to a lower temperature, and the B fraction containing glycerol added at such a lower temperature. Moreover, to mitigate the hyperosmotic effects of glycerol on sperm cells, the B fraction perhaps may be added in multiple steps, possibly so as to reduce the shock to sperm cells by subjecting sperm cells to lowered amounts of glycerol at each added glycerol step. The number of steps in which glycerol may be added may vary from perhaps as few as two steps or four steps to perhaps a great number of steps, including perhaps adding glycerol drip-wise over a period of time.

However, the interaction of glycerol with other sperm cell extender components in such procedures may entail significant drawbacks. In particular, protein components of sperm cell extenders such as egg yolk may pose complications for the handling of such extenders when present in the B fraction. This may be due to the volumetric bulk that such protein components create in a sperm cell extender. This phenomenon perhaps may be highlighted by the use of egg yolk in the B fraction of a sperm cell extender requiring centrifugation. Centrifugation may be a commonly used technique in various sperm cell applications to concentrate sperm cells. For example, in flow cytometery applications, the passage of sperm cells through a flow cytometer may tend to dilute the concentration of sperm cells to a lower concentration than that found in nature. This may be because flow cytometers typically may require entraining sperm cells in a sheath fluid, which may add to the volume of material in which sperm cells are contained. Centrifugation may return sperm cells to a higher concentration perhaps by subjecting them to centrifugal forces and concentrating them accordingly. However, centrifuging the B fraction of a sperm cell extender containing egg yolk may be problematic because the volumetric bulk of lipoproteins contained in the egg yolk may tend to compact any sperm cells that may be present in the B fraction, perhaps with the result of crushing or otherwise damaging such sperm cells.

As a result, it may perhaps be necessary to clarify the B fraction of a sperm cell extender containing protein content such as egg yolk. The goal of clarification may be to confer a lower and more uniform degree of density to such a protein-containing extender, perhaps in particular by removing clumps or other locally dense regions due perhaps to protein concentrations such as lipoprotein components of egg yolk, so that centrifugation perhaps may be accomplished without adversely compacting sperm cells. Clarification may be accomplished by any of various suitable methods, for example perhaps by filtration. However, all forms of clarification may require a dedication of resources to accomplish. For example, clarification may entail material costs such as filters or other required devices, labor costs which may tie up personnel resources that otherwise could be dedicated elsewhere, time costs which may slow down a sperm cell extension process, and financial costs related to all of the foregoing.

Moreover, simply preparing a B fraction of a sperm cell extender to contain protein content such as egg yolk may entail a degree of inherent drawbacks. Similarly to clarification, preparation of such a B fraction may entail material costs, labor costs, time costs, and financial costs. Moreover, the tendency toward spoliation over time due to the protein content of such a B fraction may further complicate its use. In particular, because such a B fraction may not keep well, it may require preparation on an as-needed basis, perhaps disrupting schedules and reducing efficiencies that could be realized if the B fraction otherwise could be prepared in large quantities ahead of time. This drawback may be particularly acute in situations where a sperm cell application may require a relatively high ratio of B fraction to A fraction. The spoliation tendencies of such a B fraction may also pose a contamination risk, for example as where the B fraction may perhaps become contaminated with bacteria due to spoliation, which may adversely affect a sperm cell application in which the contaminated B fraction inadvertently may be used. Such spoliation tendencies also may limit the use of such a B fraction in situations where environmental conditions cannot be closely monitored, for example as where it may be desired to transport the B fraction from one location to another perhaps over a large distance.

The foregoing problems regarding conventional sperm cell extenders may represent a long-felt need for an effective solution to the same. While implementing elements may have been available, actual attempts to meet this need may have been lacking to some degree. This may have been due to a failure of those having ordinary skill in the art to fully appreciate or understand the nature of the problems and challenges involved. As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field.

SUMMARY OF THE INVENTION

The inventive technology relates to methods and apparatus for reducing protein content in sperm cell extenders and may include one or more of the following features: techniques for reducing protein content in a sperm cell extender; techniques for reducing protein content in a cryoprotectant-containing B fraction of a sperm cell extender; techniques for preparing sperm cell extenders that do not require clarification; techniques for preparing low density gradient sperm cell extenders suitable for centrifugation; techniques for reducing protein content between individual steps in preparing a sperm cell extender, and techniques for establishing novel values of reduced protein content in sperm cell extenders. Accordingly, the objects of the methods and apparatus for reducing protein content in sperm cell extenders described herein address each of the foregoing problems in a practical manner. Naturally, further objects of the invention will become apparent from the description and drawings below.

DETAILED DESCRIPTION OF THE PREFERRED EMBODIMENTS

The present inventive technology includes a variety of aspects, which may be combined in different ways. The following descriptions are provided to list elements and describe some of the embodiments of the present inventive technology. These elements are listed with initial embodiments, however it should be understood that they may be combined in any manner and in any number to create additional embodiments. The variously described examples and preferred embodiments should not be construed to limit the present inventive technology to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
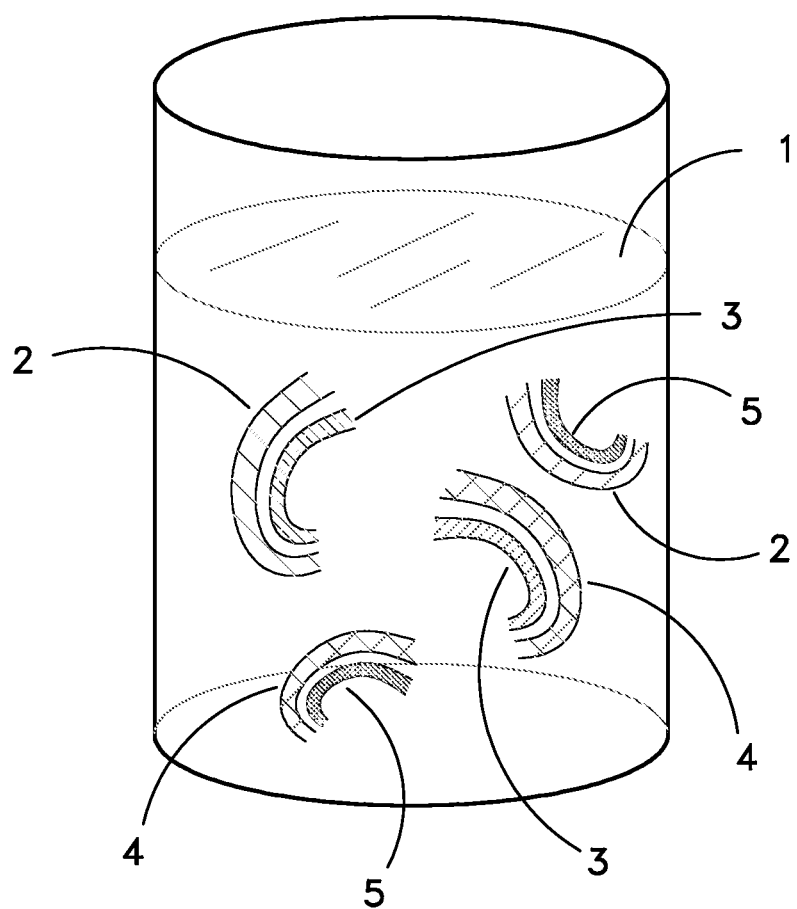
FIG. 1 is a depiction of various nascent substances in admixture relation.

Now referring primarily to FIG. 1, some embodiments may include a method for freezing sorted sperm cells compromised by a sorting event. The term sorting event may be understood to include any of a variety of events in which sperm cells are sorted based on a discrimination of characteristics retained by such sperm cells, which may include in various embodiments immunosexing techniques, buoyancy techniques, or perhaps even flow cytometery techniques. The term compromised may be understood to include any effect of a sorting event that may tend to adversely affect any desired aspect for which the sperm cells may be used, including for example sperm cell viability, sperm cell fecundity, or perhaps even sperm cell longevity. The term freezing may be understood to include any technique for preserving sperm cells that includes depressing their temperature below 0 degrees Celsius at least at some point in the technique.

Moreover, embodiments may involve obtaining a plurality of sperm cells, subjecting such a plurality of sperm cells to sorting stresses, and selecting such a plurality of sperm cells for a desired characteristic. By the term obtaining, it may be understood that any of various known techniques for obtaining sperm cells may be used, for example perhaps including manual techniques or techniques involving an artificial vagina. The term sorting stresses may be understood to include stresses that sperm cells may experience as a result of a sorting event, and subjecting sperm cells to sorting stresses may include perhaps merely accomplishing a sorting event.

A protein-containing sperm cell extender may be added to a plurality of selected sperm cells in some embodiments to form a first extended sperm cell mixture. The term sperm cell extender may be understood to include a substance that confers at least some degree of maintenance function to sperm cells. Such kinds of maintenance function may include, for example, serving to buffer sperm cells, providing nutrients to sperm cells, or perhaps even acting as a cryoprotectant for sperm cells. It may be appreciated that various kinds of sperm cell extenders may be known, perhaps including egg yolk based extenders, milk based extenders, citrate containing extenders, sodium-citrate containing extenders, Tris containing extenders, and TEST containing extenders. Moreover, the term first extended sperm cell mixture may be understood to include the combination of such a protein-containing sperm cell extender with such a plurality of selected sperm cells.

Various embodiments may further involve cooling such a first extended sperm cell mixture to create a first cooled extended sperm cell mixture. The term cooling may be understood to include reducing the temperature of a first extended sperm cell mixture to any temperature above 0 degrees Celsius. Cooling may perhaps be accomplished by any of various well-known techniques, such as perhaps refrigeration, water baths, or ice baths. In various embodiments, a first extended sperm cell mixture may be cooled perhaps to less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Certain embodiments may involve cooling a first extended sperm cell mixture to about 5 degrees Celsius. Moreover, a protein-free cryoprotectant containing sperm cell extender may be added to such a first cooled extended sperm cell mixture in some embodiments to form a second cooled extended sperm cell mixture. The term second cooled extended sperm cell mixture may be understood to include the combination of such a first cooled extended sperm cell mixture with such a protein-free cryoprotectant-containing sperm cell extender. Various embodiments may also include freezing such a second cooled extended sperm cell mixture.

A first extended sperm cell mixture in some embodiments may contain a percentage of egg yolk. This may be a function, for example, of the amount of protein contained within a protein-containing sperm cell extender added to a plurality of selected sperm cells, wherein such a protein may be egg yolk. In various embodiments, the percentage of egg yolk contained within a first extended sperm cell mixture may include more than about 0.8 percent egg yolk, more than about 1.6 percent egg yolk, more than about 3.2 percent egg yolk, or perhaps even more than about 6.4 percent egg yolk. Some embodiments may include a percentage of egg yolk contained within a first extended sperm cell mixture of about 3.2 percent.

Moreover, a second cooled extended sperm cell mixture in some embodiments, also may contain a percentage of egg yolk. This may be a function, for example, of perhaps a dilution effect of adding a protein-free cryoprotectant-containing sperm cell extender to a first cooled extended sperm cell mixture. In various embodiments, the percentage of egg yolk contained within a second cooled extended sperm cell mixture may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained with a second cooled extended sperm cell mixture of about 1.6 percent.

In some embodiments, a second cooled extended sperm cell mixture may be maintained in an unclarified state. In maintaining a second cooled extended sperm cell mixture in an unclarified state, it may be understood that such a second cooled extended sperm cell mixture may not be subject to clarification prior to any step of centrifuging. Moreover, certain embodiments may involve subjecting such a second cooled extended sperm cell mixture to centrifugation. This centrifugation may perhaps serve to concentrate sperm cells contained within such a second cooled extended sperm cell mixture, perhaps by separating such sperm cells from other components of the second cooled extended sperm cell mixture on a density basis due to the application of centrifugal force to the sperm cells. Various embodiments may further involve decanting a portion of such a centrifuged second cooled extended sperm cell mixture. For example, sperm cells concentrated by centrifugation may be concentrated largely within one area, and removing a volumetric section perhaps may include removing the volumetric section containing such concentrated sperm cells or perhaps even removing all volumetric sections not including such concentrated sperm cells.

Figure 2A:
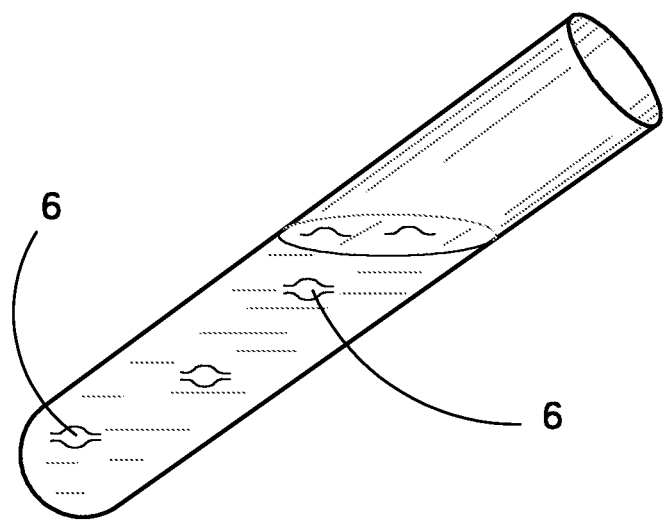
FIG. 2a is a depiction of a prior art sperm cell extender.
Figure 2B:
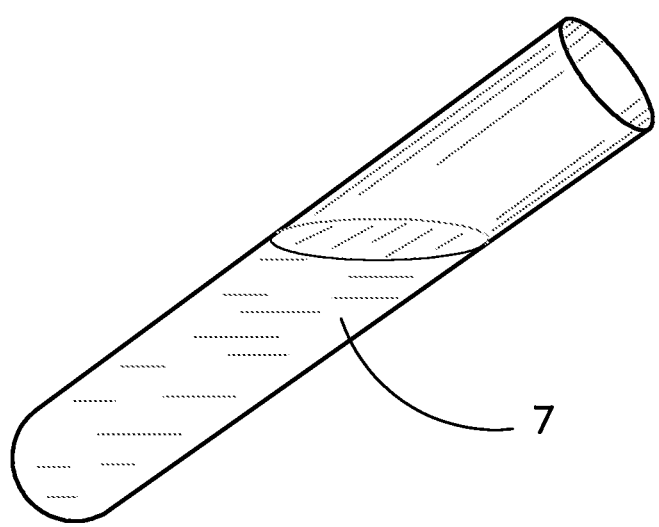
FIG. 2b is a depiction of an unclarified centrifugation medium.

Now referring primarily to FIG. 2, some embodiments may include a method for processing sorted sperm cells compromised by a sorting event. The term processing may be understood to include any event in which sperm cells are treated to change at least one characteristic of such sperm cells by at least some degree. In various embodiments, processing may include for example freezing, thawing, or perhaps even centrifuging such sperm cells.

Moreover, embodiments may involve obtaining a plurality of sperm cells, subjecting such a plurality of sperm cells to sorting stresses, and selecting such a plurality of sperm cells for a desired characteristic. Some embodiments further may include providing a protein-free sperm cell extender, providing a protein-free cryoprotectant-containing sperm cell extender, and combining such a protein-free sperm cell extender with such a protein-free cryoprotectant-containing sperm cell extender to form a cryoprotectant-containing centrifugation medium. The term centrifugation medium may be understood to include any medium conducive to sperm cells that at some point is subjected to centrifugation.

In some embodiments, combining such a protein-free sperm cell extender with such a protein-free cryoprotectant-containing sperm cell extender to form a cryoprotectant-containing centrifugation medium may be accomplished at a cool temperature. Such a cool temperature may include less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Certain embodiments may involve combining such a protein-free sperm cell extender with such a protein-free cryoprotectant-containing sperm cell extender to form a cryoprotectant-containing centrifugation medium at about 5 degrees Celsius.

A cryoprotectant-containing centrifugation medium in some embodiments may be maintained in an unclarified state. An unclarified state may be understood to include a state in which a substance may exist wherein such a substance has not been clarified. Clarification may be understood to include conferring a lower and more uniform degree of density to a substance, and perhaps may involve techniques such as filtering or straining. In maintaining a cryoprotectant-containing centrifugation medium in an unclarified state, it may be understood that such a cryoprotectant-containing centrifugation medium may not be subject to clarification prior to any step of centrifuging.

Various embodiments may further involve adding a plurality of sperm cells subjected to sorting stresses and selected for a desired characteristic to such an unclarified cryoprotectant-containing centrifugation medium, perhaps to form an unclarified cryoprotectant-containing sperm cell centrifugation medium. The term unclarified cryoprotectant-containing sperm cell centrifugation medium may be understood to include perhaps simply an unclarified cryoprotectant-containing centrifugation medium to which such a plurality of sperm cells has been added. Moreover, certain embodiments may involve subjecting such an unclarified cryoprotectant-containing sperm cell centrifugation medium to centrifugation. The term centrifugation may be understood to include applying a centrifugal force to a substance in order to separate at least two constituent components of that substance based on density. This centrifugation may perhaps serve to concentrate sperm cells contained within such an unclarified cryoprotectant-containing sperm cell centrifugation medium, perhaps by separating such sperm cells from other components of the unclarified cryoprotectant containing sperm cell centrifugation medium on a density basis due to the application of centrifugal force to the sperm cells.

Various embodiments may further involve decanting a portion of such a centrifuged unclarified cryoprotectant-containing sperm cell centrifugation medium. Decanting may be understood to include removing at least some volumetric section of a substance, perhaps such a centrifuged unclarified cryoprotectant-containing sperm cell centrifugation medium, which perhaps may be achieved by any of various well-known techniques, including for example pouring off such a volumetric section. Significantly, it may be possible to select such a volumetric section to be removed based on the amount of a centrifuged component present in such a volumetric section. For example, sperm cells concentrated by centrifugation may be concentrated largely within one area, and removing a volumetric section perhaps may include removing the volumetric section containing such concentrated sperm cells or perhaps even removing all volumetric sections not including such concentrated sperm cells.

Certain embodiments may further involve providing a protein-containing sperm cell extender and combining such a protein-containing sperm cell extender with a cryoprotectant-containing centrifugation medium to create a protein-containing cryoprotectant-containing centrifugation medium. Moreover, various embodiments may further include adding a plurality of sperm cells subjected to sorting stresses and selected for a desired characteristic to such a protein-containing cryoprotectant-containing centrifugation medium to create a protein-containing cryoprotectant-containing sperm cell centrifugation medium. Some embodiments may further involve maintaining such a protein-containing cryoprotectant-containing sperm cell centrifugation medium in an unclarified state.

Moreover, such a protein-containing cyroprotectant-containing sperm cell centrifugation medium in certain embodiments may contain a percentage of egg yolk. This may be a function, for example, of the amount of protein contained with a proteincontaining sperm cell extender combined with a cryoprotectant-containing centrifugation medium, wherein such a protein may be egg yolk. In various embodiments, the percentage of egg yolk contained within a protein-containing cyroprotectant-containing sperm cell centrifugation medium may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained within a protein-containing cyroprotectant-containing sperm cell centrifugation medium of about 1.6 percent.

In some embodiments, subjecting a protein-containing cyroprotectant-containing sperm cell centrifugation medium to centrifugation perhaps may include centrifuging such a protein-containing cyroprotectant-containing sperm cell centrifugation medium having a fraction of the percentage of egg yolk as compared to a centrifugation medium utilized in a typical method for centrifuging sorted sperm cells. Typical methods for centrifuging sorted sperm cells may be understood to include perhaps all methods for centrifuging sorted sperm cells not utilizing the novel techniques disclosed herein, and particularly may include perhaps those methods for centrifuging sorted sperm cells that may be well known in the art. Moreover, the term fraction may be understood to include an amount of egg yolk less than that contained in a centrifugation medium utilized in such a typical method. In some embodiments, such a fraction may include perhaps less than about 50 percent as compared to a centrifugation medium utilized in a typical method for centrifuging sorted sperm cells, less than about 25 percent as compared to a centrifugation medium utilized in a typical method for centrifuging sorted sperm cells, less than about 10 percent as compared to a centrifugation medium utilized in a typical method for centrifuging sorted sperm cells, less than about 5 percent as compared to a centrifugation medium utilized in a typical method for centrifuging sorted sperm cells, less than about 4 percent as compared to a centrifugation medium utilized in a typical method for centrifuging sorted sperm cells, less than about 3 percent as compared to a centrifugation medium utilized in a typical method for centrifuging sorted sperm cells, less than about 2 percent as compared to a centrifugation medium utilized in a typical method for centrifuging sorted sperm cells, or perhaps even less than about 1 percent as compared to a centrifugation medium utilized in a typical method for centrifuging sorted sperm cells. In some embodiments, such a fraction of the percentage of egg yolk as compared to a centrifugation medium utilized in a typical method for centrifuging sorted sperm cells may be a protein-containing cryoprotectant-containing sperm cell centrifugation medium having less than about 3 percent egg yolk. Some embodiments perhaps may even include centrifuging a protein-containing cryoprotectant-containing sperm cell centrifugation medium containing glycerol and having less than about 11 percent egg yolk.

Figure 3:
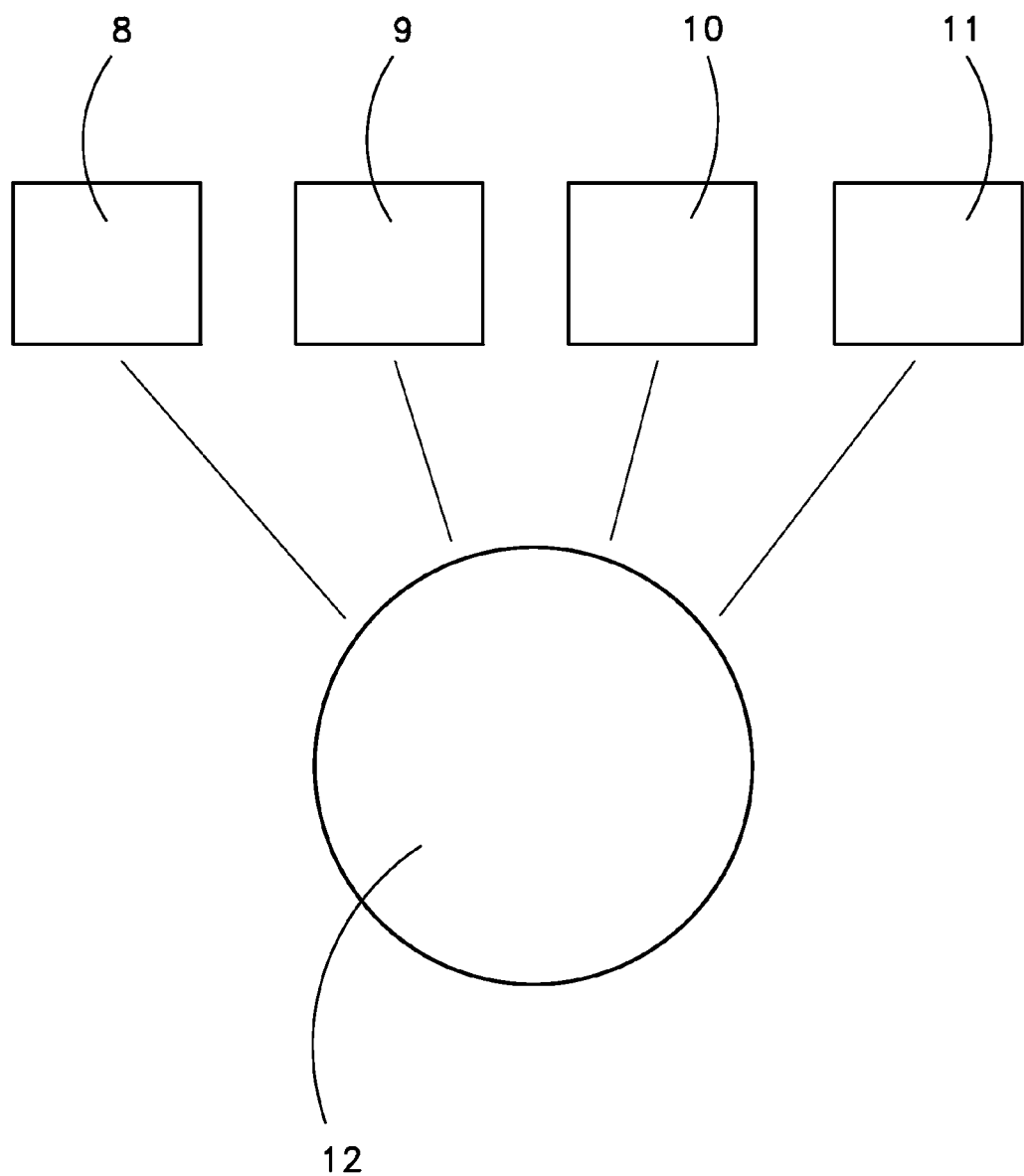
FIG. 3 is a representation of an intermediate sperm cell extender.

Now referring primarily to FIG. 3, some embodiments may involve a method for extending sorted sperm cells compromised by a sorting event. The term extending may be understood to include conferring to sperm cells at least one or more of the functionalities of a sperm cell extender.

Moreover, various embodiments may include obtaining a plurality of sperm cells, subjecting such a plurality of sperm cells to sorting stresses, and selecting such a plurality of sperm cells for a desired characteristic. Embodiments may further include establishing a protein-containing sperm cell extender having a first protein content value. Such a first protein-content value may be understood to include the protein content of such an established protein-containing sperm cell extender prior to any subsequent events that may alter such a protein content.

Various embodiments may also include adding a plurality of sperm cells subjected to sorting stresses and selected for a desired characteristic to a proteincontaining sperm cell extender having a first protein content value and also adding a protein-free sperm cell extender, perhaps including a protein-free cryoprotectantcontaining sperm cell extender, to said protein-containing sperm cell extender having a first protein content value. In various embodiments, adding a protein-free cyroprotectant-containing sperm cell extender to a protein-containing sperm cell extender having a first protein content value may be accomplished at a cool temperature. Such a cool temperature may include less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Certain embodiments may involve adding a protein-free sperm cell extender to a protein-containing sperm cell extender having a first protein content value at about 5 degrees Celsius.

Moreover, some embodiments may further include reducing a total protein content of such a protein-containing sperm cell extender having a first protein content value to a second protein content value below such a first protein content value. A total protein content perhaps simply may be the total amount of protein in a protein-containing sperm cell extender at any given time, and the term reducing a total protein content may be understood to include any of various suitable methods for accomplishing such a reduction, including perhaps directly removing protein content or perhaps simply increasing the amount of non-protein components in such a protein-containing sperm cell extender.

A first protein content value in some embodiments may include a percentage of egg yolk, for example, wherein such a protein may be egg yolk. In various embodiments, such a percentage of egg yolk may include more than about 0.8 percent egg yolk, more than about 1.6 percent egg yolk, more than about 3.2 percent egg yolk, or perhaps even more than about 6.4 percent egg yolk. Some embodiments may include a percentage of egg yolk of about 3.2 percent.

Moreover, reducing a total protein content to a second protein content value below such a first protein content value in some embodiments may include reducing a percentage of egg yolk of such a protein-containing sperm cell extender. This may be a function, for example, of perhaps a dilution effect of adding a plurality of sperm cells and adding a protein-free sperm cell extender to such a protein-containing sperm cell extender. In various embodiments, such a percentage of egg yolk of a second protein content value may include more than about 0.4 percent egg yolk, more than about 0.8 percent egg yolk, more than about 1.6 percent egg yolk, or perhaps even more than about 3.2 percent egg yolk. In some embodiments such a percentage of egg yolk of a second protein content value may be about 1.6 percent.

In some embodiments, such a protein-containing sperm cell extender having a second protein content value may be maintained in an unclarified state. In maintaining a protein-containing sperm cell extender having a second protein content value in an unclarified state, it may be understood that such a protein-containing sperm cell extender having a second protein content value may not be subject to clarification prior to any step of centrifuging. Moreover, certain embodiments may involve subjecting such a proteincontaining sperm cell extender having a second protein content value to centrifugation. This centrifugation may perhaps serve to concentrate sperm cells contained within such a protein-containing sperm cell extender having a second protein content value, perhaps by separating such sperm cells from other components of a protein-containing sperm cell extender having a second protein content value on a density basis due to the application of centrifugal force to the sperm cells. Various embodiments may further involve decanting a portion of such a centrifuged protein-containing sperm cell extender having a second protein content value. For example, sperm cells concentrated by centrifugation may be concentrated largely within one area, and removing a volumetric section perhaps may include removing the volumetric section containing such concentrated sperm cells or perhaps even removing all volumetric sections not including such concentrated sperm cells.

Various embodiments may also include adding a supplemental protein-containing sperm cell extender to a protein-containing sperm cell extender having a second protein content value and increasing a total protein content of such a protein-containing sperm cell extender to a third protein content value higher than a first protein content value. The term supplemental protein-containing sperm cell extender may be understood to include any additional protein-containing sperm cell extender that supplements a protein containing sperm cell extender having a second protein content value. The term supplement may be understood to include adding additional sperm cell extender components, for example perhaps adding an additional amount of protein.

Further, increasing a total protein content to a third protein content value in some embodiments may include increasing a percentage of egg yolk of such a protein-containing sperm cell extender. This may be a function, for example, of perhaps adding a supplemental protein-containing sperm cell extender to a protein-containing sperm cell extender having a second protein content value. In various embodiments, such a percentage of egg yolk of a third protein content value may include more than about 1 percent egg yolk, more than about 5 percent egg yolk, more than about 10 percent egg yolk, more than about 15 percent egg yolk, more than about 20 percent egg yolk, more than about 25 percent egg yolk, or perhaps even more than about 50 percent egg yolk. In some embodiments such a percentage of egg yolk of a third protein content value may be about 16.5 percent. Moreover, various embodiments may include freezing a protein-containing sperm cell extender having a third protein content value higher than a first protein content value.

Now referring to FIGS. 1-3, in various embodiments a plurality of sperm cells may include perhaps a plurality of mammalian sperm cells, including for example perhaps a plurality of bovine sperm cells, a plurality of equine sperm cells, a plurality of porcine sperm cells, a plurality of ovine sperm cells, a plurality of cervid sperm cells, a plurality of canine sperm cells, or perhaps even a plurality of delphinidae sperm cells. Moreover, some embodiments may involve selecting such a plurality of sperm cells for a desired characteristic. The term selecting may be understood to include identifying individual sperm cells based on a determination as to whether or not they possess a desired characteristic being sought. In some embodiments, selecting sperm cells for a desired characteristic may include sorting sperm cells. The term sorting may be understood to include acting to separate selected sperm cells having a desired characteristic from those sperm cells not having such a desired characteristic, perhaps including into populations of sperm cells with such a desired characteristic and populations of sperm cells without such a desired characteristic. Sorting sperm cells may be accomplished by any of a variety of suitable techniques, including perhaps immunosexing techniques, buoyancy techniques, or perhaps even flow cytometery techniques. Additionally, the term desired characteristic may be understood to include any identifiable characteristic of a sperm cell desired for a given sperm cell application. For example, in some embodiments a desired characteristic may include a sex characteristic of a sperm cell, perhaps even an Xchromosome-bearing characteristic of a sperm cell or a Y-chromosome-bearing characteristic of a sperm cell.

The term protein-containing sperm cell extender in various embodiments may be understood to include any sperm cell extender containing at least some degree of protein content. Moreover, in various embodiments a protein-containing sperm cell extender may include perhaps plant-based protein content or perhaps animal-based protein content, which may be understood to include proteins derived from plant sources and animal sources respectively. In certain embodiments, an animal-based protein-containing sperm cell extender perhaps may include a lipoprotein-containing sperm cell extender. It may be appreciated that lipoproteins may be perhaps a subclass of proteins in which at least one component of such a protein is a lipid. Such a lipoprotein content may perhaps be derived from various animal sources, including perhaps egg yolk collected from various kinds of animal eggs, perhaps including hen's eggs.

Accordingly, in certain embodiments a protein-containing sperm cell extender perhaps may include an egg-yolk-containing sperm cell extender. It may be appreciated that the precise egg yolk content of such an egg-yolk-containing sperm cell extender may be varied depending on the needs of a particular application for which sperm cells may be used. However, in some embodiments an egg yolk content of an egg-yolk-containing sperm cell extender may include less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, less than about 10 percent egg yolk, or perhaps even less than about 5 percent egg yolk. In certain embodiments, an egg yolk content of an egg-yolk-containing sperm cell extender may be about 20 percent egg yolk.

A cryoprotectant may be included as a constituent part of a sperm cell extender in various embodiments. Accordingly, a sperm cell extender in various embodiments may include perhaps a protein-free cryoprotectant-containing sperm cell extender or perhaps even a protein-containing cyroprotectant-containing sperm cell extender. It may be appreciated that various well-known cryoprotectants perhaps may be appropriate for such addition to a sperm cell extender. In various embodiments, such a cryoprotectant perhaps may include glycerol. It may be appreciated that the precise glycerol content of such a glycerol-containing sperm cell extender may be varied depending on the needs of a particular application for which sperm cells may be used. However, in some embodiments a glycerol-containing sperm cell extender may have more than about 3 percent glycerol, more than about 6 percent glycerol, more than about 12 percent glycerol, or perhaps even more than about 24 percent glycerol. In certain embodiments, a glycerol content of a glycerol-containing sperm cell extender may be about 6 percent.

Moreover, in certain embodiments a protein-free cryoprotectant-containing sperm cell extender may be added to a substance in an equal volume to that substance, perhaps including accomplishing such an addition in multiple steps. For example, adding a protein-free cryoprotectant-containing sperm cell extender to a first cooled extended sperm cell mixture may involve adding such a protein-free cryoprotectant-containing sperm cell extender having a volume equal to a volume of such a first cooled extended sperm cell mixture, perhaps in two or more steps. Similarly, combining a protein-free cryoprotectant-containing sperm cell extender and a protein-free sperm cell extender may involve adding such a protein-free cryoprotectant-containing sperm cell extender in a volume equal to a volume of such a protein-free sperm cell extender, perhaps in two or more steps. Further, adding a protein-free cryoprotectant-containing sperm cell extender to a protein-containing sperm cell extender may involve adding such a protein-free cryoprotectant-containing sperm cell extender having a volume equal to a volume of such a protein-containing sperm cell extender, perhaps in two or more steps.

A protein-free cryoprotectant-containing sperm cell extender in certain embodiments may include a low density gradient cryoprotectant-containing sperm cell extender. Accordingly, in some embodiments adding a protein-free cryoprotectant-containing sperm cell extender to a first cooled extended sperm cell mixture may involve adding a low density gradient cryoprotectant-containing sperm cell extender to such a first cooled extended sperm cell mixture. Further, in some embodiments providing a protein-free cryoprotectant-containing sperm cell extender may involve providing a low density gradient cryoprotectant-containing sperm cell extender. Also, in some embodiments adding a protein-free cryoprotectant-containing sperm cell extender to a protein-containing sperm cell extender may involve adding a low density gradient cryoprotectant-containing sperm cell extender to such a protein-containing sperm cell extender.

The term low density gradient may be understood to include a sperm cell extender having minimal density variations throughout its volume. In some embodiments, a low density gradient cryoprotectant-containing sperm cell extender may perhaps include a substantially liquid cryoprotectant-containing sperm cell extender. The term substantially liquid may be understood to include a cryoprotectant-containing sperm cell extender wherein all constituent parts of such a cryoprotectant-containing sperm cell extender are in a substantially liquid state. In various embodiments, a low density gradient cryoprotectant-containing sperm cell extender may perhaps include a centrifugationefficient cryoprotectant-containing sperm cell extender. The term centrifugation-efficient may be understood to include a cryoprotectant-containing sperm cell extender having properties conducive to centrifugation, for example perhaps including clearly demarcated density differences in its constituent parts or perhaps even a lack of localized higher density regions that may pose a compaction risk to certain of its constituent parts. In various embodiments, a low density gradient cryoprotectant-containing sperm cell extender may perhaps include a substantially uniform density cryoprotectant-containing sperm cell extender, which may be understood to include a minimal number of localized areas of higher density, perhaps even approaching no areas of localized higher density. In various embodiments, a low density gradient cryoprotectant-containing sperm cell extender may perhaps include a cryoprotectant-containing sperm cell extender with substantially no sperm cell compaction particles. The term sperm cell compaction particle may be understood to include any particle or group of particles joined together that may tend to compact sperm cells to a damaging degree when subjected to various types of forces, perhaps including centrifugal forces. In various embodiments, a low density gradient cryoprotectant-containing sperm cell extender may perhaps include a low viscosity cryoprotectant-containing sperm cell extender. The term low viscosity may be understood to include a viscosity of a cryoprotectant-containing sperm cell extender sufficient to permit its constituent parts to slip past each other without tending toward the compaction of any one constituent part by any other constituent part.

Various embodiments may include adjusting a sperm cell concentration of a substance to a pre-freeze sperm cell concentration. The term pre-freeze sperm cell concentration may be understood to include a concentration of sperm cells at which such sperm cells may subsequently be frozen. For example, some embodiments may involve adjusting a sperm cell concentration of a second cooled extended sperm cell mixture to a pre-freeze sperm cell concentration, while other embodiments may involve adjusting a sperm cell concentration of a protein-containing sperm cell extender having a second protein content value to a pre-freeze sperm cell concentration. In various embodiments, adjusting to such a pre-freeze sperm cell concentration may include adding a protein containing sperm cell extender, including for example perhaps adding a protein containing sperm cell extender to a second extended sperm cell mixture or perhaps adding a supplemental protein-containing sperm cell extender to a protein-containing sperm cell extender having a second protein content value.

In various embodiments, adjusting a sperm cell concentration to a pre-freeze sperm cell concentration may involve adjusting a sperm cell concentration to a species-appropriate pre-freeze concentration. The term species-appropriate pre-freeze sperm cell concentration my be understood to include a concentration of sperm cells at which such sperm cells may subsequently be frozen that is appropriate for the species of animal from which such sperm cells were obtained. It may be appreciated that a species-appropriate pre-freeze sperm cell concentration may be known for a variety of animal species, or perhaps even may determined through routine empirical observation over a number of freezing events. In some embodiments, a species-appropriate pre-freeze sperm cell concentration may include a bovine pre-freeze sperm cell concentration, an equine pre-freeze sperm cell concentration, a porcine pre-freeze sperm cell concentration, an ovine pre-freeze sperm cell concentration, a cervid pre-freeze sperm cell concentration, a canine pre-freeze sperm cell concentration, or perhaps even a delphinidae sperm cell concentration. Moreover, in various embodiments a species-appropriate pre-freeze sperm cell concentration may include less than about 100 million sperm cells per milliliter, less than about 50 million sperm cells per milliliter, less than about 40 million sperm cells per 22 milliliter, less than about 30 million sperm cells per milliliter, less than about 20 million sperm cells per milliliter, less than about 15 million sperm cells per milliliter, less than about 10 million sperm cells per milliliter, less than about 5 million sperm cells per milliliter, or perhaps even less than about 2 million sperm cells per milliliter. In certain embodiments, perhaps including those involving a bovine pre-freeze sperm cell concentration, a species-appropriate pre-freeze concentration may be about 10 million sperm cells per milliliter.

Adjusting a sperm cell concentration to a pre-freeze sperm cell concentration in some embodiments may include establishing a pre-freeze egg yolk content. For example, adjusting a sperm cell concentration of a second cooled extended sperm cell mixture to a pre-freeze sperm cell concentration may include establishing a pre-freeze egg yolk content of such second extended sperm cell mixture. Similarly, adjusting a sperm cell concentration of a protein-containing sperm cell extender having a second protein content value to a pre-freeze sperm cell concentration may include establishing a pre-freeze egg yolk content of such a protein-containing sperm cell extender. A pre-freeze egg yolk content may be understood to include perhaps simply an egg yolk content of a substance at a pre-freeze concentration. In various embodiments, a pre-freeze egg yolk content may include an egg yolk content within a percentage of the egg yolk content of a typical method for freezing sorted sperm cells. Such a typical method for freezing sorted sperm cells may be understood to include perhaps all methods for freezing sorted sperm cells not utilizing the novel techniques disclosed herein, and particularly may include perhaps those methods for freezing sorted sperm cells that may be well known in the art. In various embodiments, a pre-freeze egg yolk content may include may include perhaps within about 50 percent of the pre-freeze egg yolk content of a typical method for freezing sorted sperm cells, within about 25 percent of the pre-freeze egg yolk content of a typical method for freezing sorted sperm cells, within about 20 percent of the pre-freeze egg yolk content of a typical method for freezing sorted sperm cells, within about 15 percent of the pre-freeze egg yolk content of a typical method for freezing sorted sperm cells, within about 10 percent of the pre-freeze egg yolk content of a typical method for freezing sorted sperm cells, within about 5 percent of the pre-freeze egg yolk content of a typical method for freezing sorted sperm cells, within about 2 percent of the pre-freeze egg yolk content of a typical method for freezing sorted sperm cells, and perhaps even within about 1 percent of the pre-freeze egg yolk content of a typical method for freezing sorted sperm cells.

Moreover, in certain embodiments a pre-freeze egg yolk content perhaps may be established at an absolute value of less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, or perhaps even less than about 10 percent egg yolk. In some embodiments, a pre-freeze egg yolk content may be established at about 16.5 percent.

The use of a sterile sperm cell extender may be involved in certain embodiments. For example, in various embodiments a protein-free sperm cell extender may include a sterile protein-free sperm cell extender, and a protein-free cryoprotectant-containing sperm cell extender may include a sterile protein-free cryoprotectant-containing sperm cell extender.

Now with further reference primarily to FIG. 1, various embodiments may include an incipient admixture (1), which in various embodiments perhaps may include an incipient compromised sorted sperm cell admixture. An admixture may be understood to include two or more substances in a state of being mixed, and an incipient admixture (1) may be understood to include an admixture that is less than completely saturated with respect to any two constituent components capable of being mixed. In various embodiments, an incipient admixture (1) may include perhaps an admixture that has achieved less than 50 percent saturation, less than 25 percent saturation, less than 10 percent saturation, less than 5 percent saturation, less than 2 percent saturation, or perhaps even less than 1 percent saturation.

Some embodiments may include two or more nascent substances in incipient admixture relation. An incipient admixture relation may be understood to include two or more substances related by existing together in an incipient admixture (1). A nascent substance may be understood to include a substance that exists in a less than saturated combination with another substance in incipient admixture relation. Moreover, an admixture in some embodiments may include two or more nascent components, wherein such a component may be understood to be a component of an incipient admixture (1). For example, various embodiments may include a nascent plurality of sperm cells selected for a desired characteristic (2) in incipient admixture relation, a nascent protein-free sperm cell extender component in incipient admixture relation (3), a nascent protein free cryoprotectant-containing sperm cell extender component in incipient admixture relation (4), or perhaps even a nascent protein-containing sperm cell extender component in incipient admixture relation (5).

In some embodiments, a nascent substance may include a substance proximately located in a substantially uncombined state to at least one component of an incipient admixture (1). The term proximately located may be understood to include a location of such a nascent substance near enough to such a component of an incipient admixture (1) so as to permit a combination of the two. The term substantially uncombined state may be understood to include the existence of such a nascent substance in a state of mostly unsaturated combination with such a component of an incipient admixture (1), which may include perhaps existing as more than 50 percent uncombined, existing as more than 75 percent uncombined, existing as more than 90 percent uncombined, existing as more than 95 percent uncombined, or perhaps even existing as more than 99 percent uncombined. For example, various embodiments may include a plurality of sperm cells selected for a desired characteristic proximately located in a substantially uncombined state to at least one component of an incipient admixture (1), a protein-free sperm cell extender component proximately located in a substantially uncombined state to at least one component of an incipient admixture (1), a protein-free cryoprotectant-containing sperm cell extender component proximately located in a substantially uncombined state to at least one component of an incipient admixture (1), or perhaps even a protein-containing sperm cell extender component proximately located in a substantially uncombined state to at least one component of an incipient admixture (1).

Moreover, certain embodiments may include a barrier-free zone between a nascent substance and a component of an incipient admixture (1). Such a barrier free zone may be understood to include a zone containing no elements that may tend to prevent the combination of such a nascent substance and such a component of an incipient admixture (1). Some embodiments may even involve an induced combination force to which a nascent substance and a component of an incipient admixture (1) may be responsive. Such an induced combination force may be understood to include any force tending to induce a combination of two or more substances in incipient admixture relation. Examples of an induced combination force may include perhaps a density related force, a concentration-related force, or perhaps even simple hydrodynamic forces generated by placing various liquids in a container. The term responsive may be understood to include any effect on such a nascent substance or component of an incipient admixture (1) caused by such an induced combination force.

Moreover, an incipient admixture (1) in some embodiments may contain an egg yolk content. This may be a function, for example, of the amount of protein in a nascent protein-containing sperm cell extender component, perhaps wherein such protein may be egg yolk. In various embodiments, the percentage of egg yolk contained within an incipient admixture may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained with an incipient admixture (1) of about 1.6 percent.

In various embodiments, an incipient admixture (1) may include an unclarified incipient admixture (1). Various embodiments also may include a cool incipient admixture. In some embodiments, a cool incipient admixture may be an incipient admixture (1) at a temperature of less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Moreover, in some embodiments a cool incipient admixture may be an admixture at about 5 degrees Celsius.

Now with further reference primarily to FIG. 2, some embodiments may include a compromised sorted sperm cell processing medium. The term processing medium may be understood to include any medium conducive to sperm cells in which sperm cells may be placed to undergo processing. Moreover, embodiments also may include a plurality of sperm cells selected for a desired characteristic, an unclarified protein-free sperm cell extender component, an unclarified protein-free cryoprotectant-containing sperm cell extender component, and an unclarified centrifugation medium (7) in which said plurality of sperm cells selected for a desired characteristic, said unclarified protein-free sperm cell extender component, and said unclarified protein-free cryoprotectant-containing sperm cell extender component are suspended. The term unclarified may be understood to include a substance maintained in an unclarified state, and the term unclarified state may be understood to include a state in which a substance may exist wherein such a substance has not been clarified. The term centrifugation medium may be understood to include any medium conducive to sperm cells that at some point is subjected to centrifugation.

Certain embodiments may further include an unclarified protein-containing sperm cell extender component suspended in an unclarified centrifugation medium (7). Moreover, such an unclarified centrifugation medium (7) in some embodiments may contain an egg yolk content. This may be a function, for example, of perhaps the amount of protein in such an unclarified protein-containing sperm cell extender component, perhaps wherein such protein may be egg yolk. In various embodiments, the percentage of egg yolk contained within an unclarified centrifugation medium (7) may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained with an unclarified centrifugation medium (7) of about 1.6 percent. Moreover, in certain embodiments an unclarified centrifugation medium (7) may contain at least some glycerol and have less than about 11 percent egg yolk.

Moreover, in certain embodiments an unclarified centrifugation medium (7) may perhaps include a cool unclarified centrifugation medium (7). Such a cool unclarified centrifugation medium (7) perhaps may include an unclarified centrifugation medium (7) at a temperature of less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. In some embodiments, a cool unclarified centrifugation medium (7) may include an unclarified centrifugation medium (7) at a temperature of about 5 degrees Celsius.

In some embodiments, an unclarified centrifugation medium (7) may perhaps have a minimized number of localized high density regions (6), including perhaps even no localized high density regions (6). The term localized may be understood to include a region of an unclarified centrifugation medium (7) that may be concentrated within a small volume of such an unclarified centrifugation medium (7), including perhaps a volume of less than 3 percent, less that 2 percent, less 1 percent, less than 0.05 percent, or perhaps even less than 0.01 percent of the total volume of an unclarified centrifugation medium (7). The term localized high density region (6) may be understood to include localized regions of an unclarified centrifugation medium (7) having a substantially higher density than surrounding regions, including perhaps more than 10% of a surrounding density, more than 20% of a surrounding density, more than 30% of a surrounding density, more than 40% of a surrounding density, more than 50% of a surrounding density, more than 100% of a surrounding density, more than 200% of a surrounding density, more than 300% of a surrounding density, more than 400% of a surrounding density, or perhaps even more than 500% of a surrounding density.

Now with further reference primarily to FIG. 3, certain embodiments may include an intermediate compromised sorted sperm cell extension medium. A sperm cell extension medium may be understood to include any medium conducive to sperm cells in which sperm cells may be placed for extension. The term intermediate may be understood to include a sperm cell extension medium representing an intermediate step in a process of treating sperm cells. For example, in various embodiments such an intermediate step perhaps may include adding a cryoprotectant to a previously prepared sperm cell medium, adding protein content to a previously prepared sperm cell medium, or perhaps centrifuging a previously prepared sperm cell medium.

Moreover, further embodiments may include a plurality of sperm cells selected for a desired characteristic (8), a protein-free sperm cell extender component (9), a protein-free cryoprotectant-containing sperm cell extender component (10), and a protein-containing sperm cell extender component (11). Certain embodiments also may include a total protein content not exceeding about 1.6 percent (12). This may be a function, for example, of perhaps the amount of protein in a protein-containing sperm cell extender component of such an intermediate sperm cell extension medium. In some embodiments, the protein in a protein-containing sperm cell extender perhaps may be egg yolk. Accordingly, a total protein content not exceeding about 1.6 percent perhaps may include an egg yolk content not exceeding about 1.6 percent.

Certain embodiments may also include a cooled intermediate extension medium in which a plurality of sperm cells selected for a desired characteristic (8), protein-free sperm cell extender component (9), a protein-free cryoprotectant-containing sperm cell extender component (10), and a protein-containing sperm cell extender component (11) may be suspended. In some embodiments, such a cooled intermediate extension medium may include an intermediate extension medium at a temperature of perhaps less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. In certain embodiments such a cooled intermediate extension medium may have a temperature of about 5 degrees Celsius.

Several advantages may attend the inventive technology. In particular, the use of a protein-free cryoprotectant-containing sperm cell extender in various embodiments may represent a significant improvement over previous sperm cell extenders. For example, the addition of such a protein-free cryoprotectant-containing sperm cell extender to other sperm cell extenders may reduce clumps or other locally dense regions due perhaps to lower concentrations of such proteins, perhaps including egg yolk. This may reduce or perhaps even eliminate the compaction of sperm cells in certain applications, for example centrifuging, that may cause damage to sperm cells. Additionally, the reduction of such clumps in a sperm cell extender may eliminate the need to clarify such an extender, resulting in related materials savings, labor savings, time savings, and financial savings. Further, a protein-free cryoprotectant-containing sperm cell extender may be less susceptible to the effects of spoliation. This may allow such a sperm cell extender to be prepared in large quantities ahead of time, rather than on an as-needed basis. Additionally, mitigating the effects of spoliation may reduce the risk of contamination by bacteria. Further, because such a sperm cell extender perhaps may be less sensitive to environmental conditions, it may be more able to be transported over large distances where environmental conditions may vary.

Accordingly, such a protein-free cryoprotectant-containing sperm cell extender may be an effective B fraction of a sperm cell extender in various applications. Moreover, it may be that use of such a protein-free cryoprotectant-containing sperm cell extender may not significantly adversely impact the effectiveness of a sperm cell extender in which it used. For example, in embodiments relating to artificial insemination techniques, the use of such a sperm cell extender perhaps may yield results that are not significantly different than those achieved with the use of typical sperm cell extenders. In particular, pregnancy rates achieved with such a sperm cell extender in various embodiments perhaps may be comparable to those achieved with typical sperm cell extenders, including perhaps even being statistically comparable (P>0.05) in various embodiments.

Several examples may be reported using the inventive technology as herein described. Importantly, these examples should be understood to represent only some embodiments of the inventive technology. Accordingly, it may be appreciated that these examples should not be construed as limiting the scope of the inventive technology herein described.

Example 1

One possible procedure for collecting and processing sorted sperm involving a B-fraction of an extender containing egg yolk may be as follows. Tris-A catch medium (2-ml) may be deposited in a 50-ml Falcon tube. Sorted sperm may be collected into the 50-ml Falcon tube over the course of approximately 1 hour for a total sorted volume of 12.5-ml. This volume may be non-glycerol containing and may be referred to as the A-fraction. The percent of egg yolk in the A-fraction for this example is 3.2% [(2-ml "Catch")/(12.5-ml total volume)×(20% egg yolk "Catch")=3.2%)]. The 3.2% egg yolk admixture may be cooled to 5° C. over perhaps 90-min. Following the cooling period, an equal volume of glycerol-containing 20% egg yolk extender (B-fraction; 12% glycerol) may be added stepwise as 2 equal fractions at perhaps 15-min intervals. Cooled sorted sperm, now contained in this example in an 11.6% egg yolk AB extender [((12.5-ml A-fraction)×(3.2% egg yolk)+(12.5-ml B-fraction)×(20% egg yolk))/25-ml total volume=11.6% egg yolk] may be centrifuged for concentration. This method of adding the glycerol-containing extender to cooled sperm may avoid over extension of sperm pellets that may occur when non-sperm containing droplets are perhaps collected in the sorting process, if the sperm pellet is left in too much volume, and may assure that the final glycerol content is always 6%. A 200-μl sperm pellet may remain after removal of the supernatant. Sperm pellets from the same male may be pooled and total volume may be determined by weight. The number of total sorted sperm may be determined, perhaps with multiple hemacytometer counts, and the sperm concentration of the pellet may be adjusted to a desired freezing concentration, perhaps with 20% egg yolk AB extender.

In this example, if the sperm concentration in the 12.5-ml sorted volume is $1\times10^6$ sperm/ml, representing $12.5\times10^6$ total sperm, and the post-centrifuge recovery rate is 85%, then the sperm concentration in the 200-μl sperm pellet is ~$53\times10^6$ sperm/ml ($10.6\times10^6$ total sperm). If a freezing concentration of $10\times10^6$ sperm/ml is desired for this methodology, then 860-μl of 20% egg yolk AB extender may be added to the 200-μl sperm pellet. Based on this model, the final egg yolk percent for freezing sorted sperm is 18.4% [((0.200-ml sperm pellet)×(11.6% egg yolk)+(0.860-ml AB extender)×(20% egg yolk))/1.06-ml total volume=18.4% final egg yolk].

Using the above example, but substituting 0% egg yolk B-extender in place of 20% egg yolk B-extender, the percent of egg yolk contained in the 25-ml volume to be centrifuged is 1.6% [((12.5-ml A-fraction)×(3.2% egg yolk)+(12.5-ml B-fraction)×15 (0% egg yolk))/25-ml total volume=1.6% egg yolk]. If the sperm pellet in this example is adjusted to a final freezing concentration of $10\times10^6$ sperm/ml with 20% egg yolk AB extender, the final egg yolk percent is 16.5% [((0.200-ml sperm pellet)×(1.6% egg yolk)+(0.860-ml AB-extender)×(20% egg yolk))+1.06-ml total volume=16.5% egg yolk].

Accordingly, it may be seen that the final egg yolk percentage may perhaps vary only slightly between the two different B-fraction extenders. When using the 0% egg yolk B-extender, the final egg yolk percentage may be less when higher sperm concentrations (>$10\times10^6$ sperm/ml) are desired.

Example 2

A further example may be reported as follows. Sperm were studied from first ejaculates obtained from 6 bulls and the study was replicated three times. Sperm for this study were not sorted but were subjected to Hoechst 33342 staining and extreme dilution as occurs during sorting. The objective was to compare post-thaw motility of sperm that received glycerol-containing extender (B-fraction) with or without egg yolk. An additional objective was to identify the optimal glycerol content needed for sorted sperm. Therefore, 3, 4, 5 and 6% final glycerol content was studied in both 0 and 20% egg yolk containing B-fraction extender. Sperm frozen in 0.25-ml straws were thawed in a 37° C. water bath for 30 sec and were incubated at 37° C. Visual estimates of total motility were determined by 2 observers, blind to treatment, at 30 and 120 min of incubation.

Figure 4:
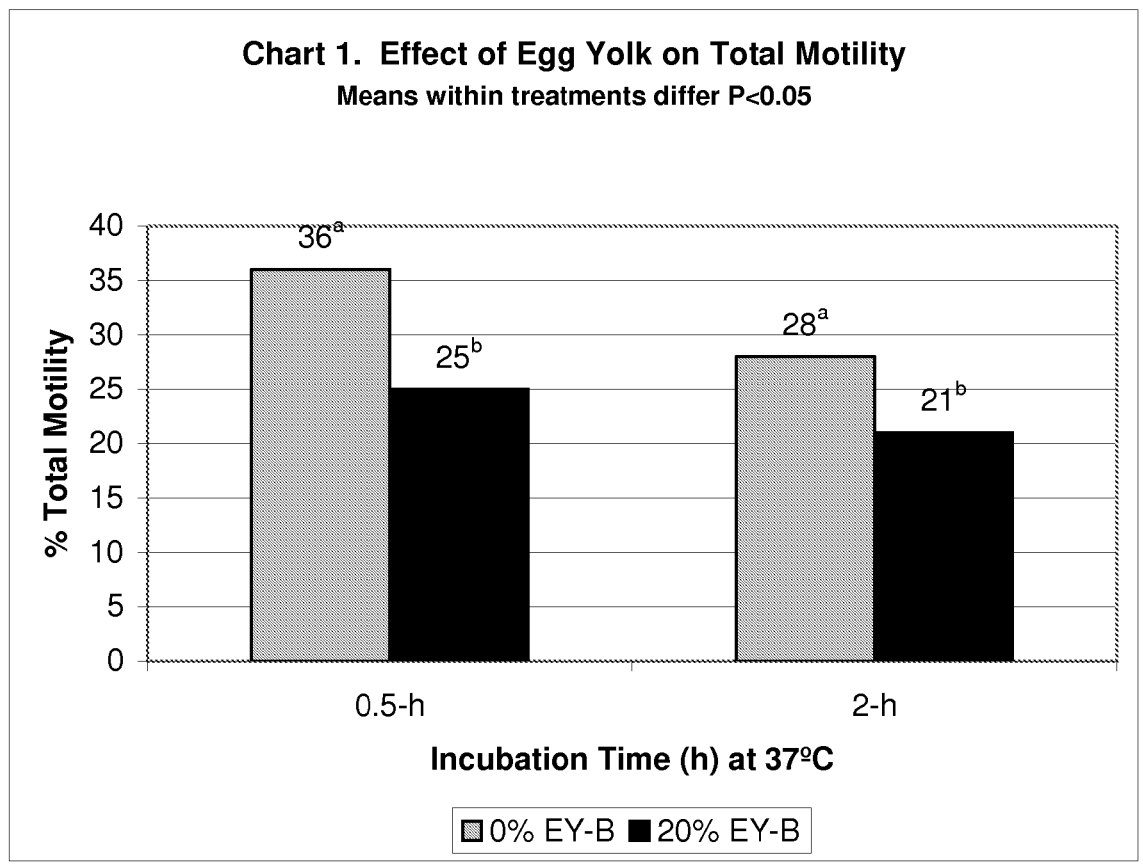
FIG. 4 is a chart showing the effect of egg yolk on total motility.

The exclusion of egg yolk in the B-fraction extender did not adversely affect post-thaw sperm motility. In fact, motility was statistically higher for sperm processed in B-10 fraction extender without egg yolk as compared to that with 20% egg yolk (P<0.05) at both incubation times. See FIG. 4.

Figure 5:
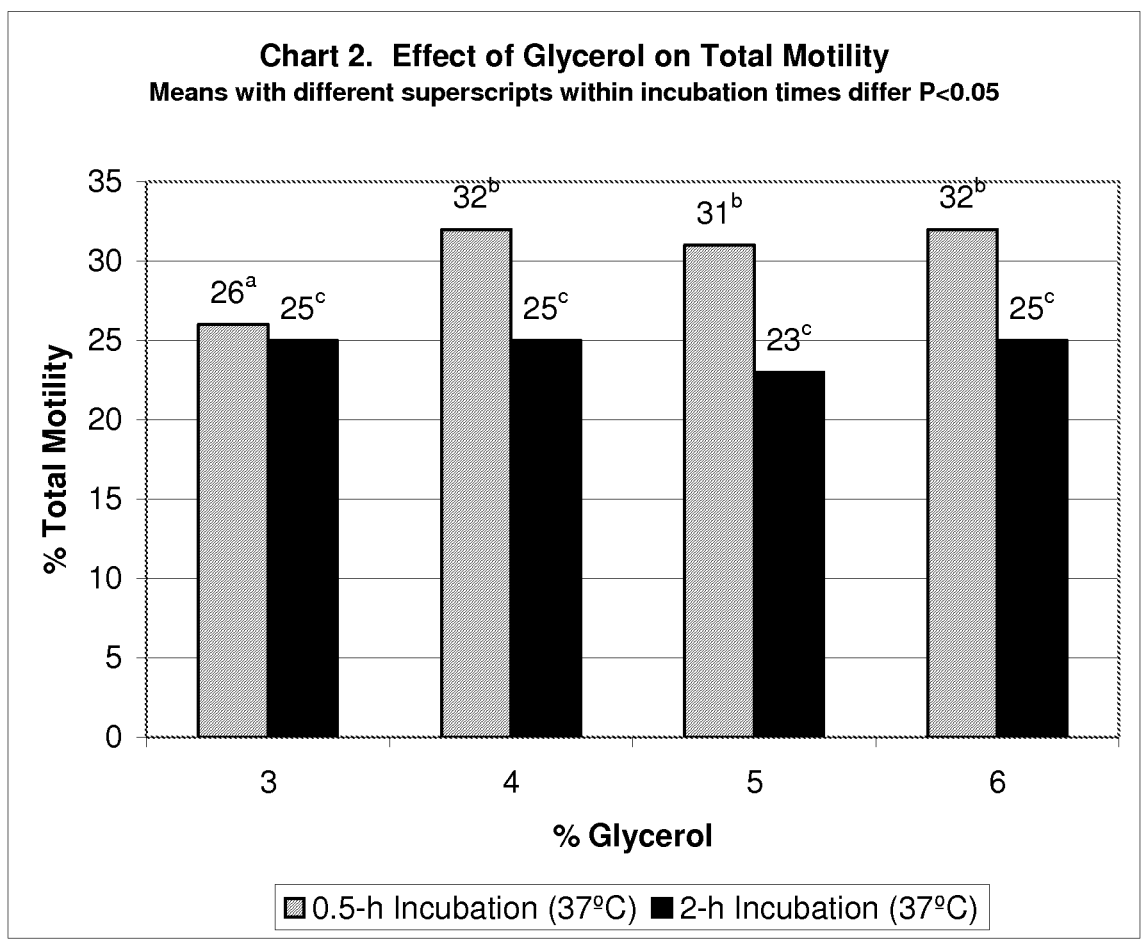
FIG. 5 is a chart showing the effect of glycerol on total motility.

A final glycerol concentration of 3% resulted in statistically lower motilities at 30-min and 120-min after thawing, while motilities were higher and did not differ as a function of 4-6% glycerol. See FIG. 5. From this example, it perhaps may be concluded that 3% glycerol did not provide adequate cryoprotection for sorted sperm. Since motilities did not differ between 4-6% glycerol, and the provision of adequate cryoprotection may be desirable (which may differ between bulls), a final concentration of 6% glycerol for sex sorted sperm cryopreservation may be appropriate.

Example 3

Another example may be reported as follows. An objective was to compare 30-day pregnancy rate in Holstein heifers inseminated with X-chromosome bearing sperm that were processed with 0% egg yolk glycerol (12%) containing extender to that containing 20% egg yolk.

X-chromosome bearing sperm from each of 2 bulls were isolated on the basis of DNA content using a flow cytometer. Sorted sperm were collected in 50-ml plastic tubes containing 2-ml of 20% egg yolk-TRIS extender without glycerol until each tube contained 12.5-ml and approximately 12 million sperm. Sorted sperm were cooled (5° C.) over 90 minutes.

After cooling, sperm-containing sort tubes (50-ml Falcon) were evenly separated and glycerol-containing extender (B-fraction) added. Cooled sperm received either B-fraction extender containing 0% egg yolk or 20% egg yolk. Tubes containing sorted sperm (25-ml total volume) were then centrifuged at 850×g for 20-minutes at 5° C. Supernatant was removed, leaving sorted sperm in approximately 200-μl pellets. Like sperm pellets were pooled and adjusted to $10 \times 10^6$ sperm/ml with 20% egg yolk-AB medium (6% final glycerol content). Final egg yolk percentage in the product varied by sorting day (range: 16.5-18.2%). Sperm ($2 \times 10^6$) were packaged into 0.25-ml coded straws to ensure treatments were blind to AI technicians, placed on freezing racks and cryopreserved in $LN_2$ vapor. An equal number of straws from each bull and treatment were placed into goblets and attached to aluminum canes.

Sperm post-thaw motility was determined using "Track" motility after 30-min of incubation at 37° C. The mean percentage of progressively motile sperm for the freeze codes processed with 20% egg yolk B-fraction extender was 44% and that for the 0% egg yolk B-fraction extender was 43%.

119 non-synchronized Holstein heifers were balanced across the different egg yolk-media and 2 Holstein bulls. Insemination occurred 12 or 24 hours after observed standing estrus. Three inseminators were used in this example. Approximately 1 month after insemination, pregnancy was determined using ultrasound. Data were subjected to ANOVA.

Pregnancy rate did not differ (P>0.05) between sorted sperm processed with 0% egg yolk-"B" fraction extender to that for 20% egg yolk-"B" fraction extender. See Table 1.

Actual pregnancy rates were similar for bulls and AI technicians (P>0.05), and there were no statistical interactions. Numerically, the pregnancy rate for bull 52H0039 as higher than for bull 52H0038. See Table 2. A larger sampling of the population may have resulted in a significant difference in pregnancy rate between the two bulls. It may be important to note for this example that the 95% confident intervals (C1) are large.

TABLE 1

0% Egg Yolk vs. 20% Egg Yolk "B" Extender Field Trial by Treatment

| Treatment | (n) | Pregnant (%) ± S.E.M. | 95% CI |
|---|---|---|---|
| 0% Egg Yolk-"B" | 59 | 56 ± 0.065 | 43-68 |
| 20% Egg Yolk-"B" | 60 | 55 ± 0.065 | 42-67 |

Actual means are presented.
Bulls (n = 2), AI technicians (n = 3) and Treatments (n = 2) were similar (P > 0.05).

TABLE 2

0% Egg Yolk vs. 20% Egg Yolk "B" Extender Field Trial by Bull

| Bull # | (n) | Pregnant (%) ± S.E.M. | 95% CI |
|---|---|---|---|
| 52H0039 | 60 | 62 ± 0.063 | 49-73 |
| 52H0038 | 59 | 49 ± 0.065 | 38-62 |

Actual means are presented.
Bulls (n = 2) were similar (P > 0.05).

As may be easily understood from the foregoing, the basic concepts of the present invention may be embodied in a variety of ways. It involves both sperm cell extending techniques as well as devices to accomplish the appropriate sperm cell extension. In this application, the sperm cell extending techniques are disclosed as part of the results shown to be achieved by the various devices described and as steps that are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included herein is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and roader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element that causes that action. Similarly, each physical element disclosed should be understood to encompass a disclosure of the action that that physical element facilitates. Regarding this last aspect, as but one example, the disclosure of an "extender" should be understood to encompass disclosure of the act of "extending"—whether explicitly discussed or not—and, conversely, were there effectively disclosure of the act of "extending", such a disclosure should be understood to encompass disclosure of an "extender" and even a "means for extending" Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the Information Disclosure Statement or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the sperm cell extender devices as herein disclosed and described, ii) the related methods disclosed and described, iii) similar, quivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. A method for extending sorted sperm cells compromised by a sorting event comprising the steps of:
   obtaining a plurality of sperm cells;
   subjecting said plurality of sperm cells to sorting stresses;
   selecting said plurality of sperm cells for a desired characteristic;
   adding said plurality of sperm cells subjected to sorting stresses and selected for a desired characteristic to a protein-containing sperm cell extender having a first protein content value;
   adding a protein-free sperm cell extender to said protein-containing sperm cell extender having a first protein content value; and
   reducing a total protein content of said protein-containing sperm cell extender to a second protein content value below said first protein content value.

2. A method for extending sorted sperm cells compromised by a sorting event as described in claim 1, wherein the protein-containing sperm cell extender having a first protein content value comprises an egg-yolk containing sperm cell extender having a percentage of egg yolk selected from the group consisting of more than about 0.8 percent egg yolk, more than about 1.6 percent egg yolk, more than about 3.2 percent egg yolk, and more than about 6.4 percent egg yolk.

3. A method for extending sorted sperm cells compromised by a sorting event as described in claim 1, wherein said step of adding a protein-free sperm cell extender to said protein-containing sperm cell extender having a first protein content value comprises the step of adding a low density gradient sperm cell extender to said protein-containing sperm cell extender having a first protein content value.

4. A method for extending sorted sperm cells compromised by a sorting event as described in claim 3, wherein said step of adding a low density gradient cryoprotectant-containing sperm cell extender to said protein-containing sperm cell extender having a first protein content value comprises the step of adding a substantially liquid cryoprotectant-containing sperm cell extender to said protein-containing sperm cell extender having a first protein content value.

5. A method for extending sorted sperm cells compromised by a sorting event as described in claim 3, wherein said step of adding a low density gradient cryoprotectant-containing sperm cell extender to said protein-containing sperm cell extender having a first protein content value comprises the step of adding a substantially uniform density cryoprotectant-containing sperm cell extender to said protein-containing sperm cell extender having a first protein content value.

6. A method for extending sorted sperm cells compromised by a sorting event as described in claim 3, wherein said step of adding a low density gradient cryoprotectant-containing sperm cell extender to said protein-containing sperm cell extender having a first protein content value comprises the step of adding a cryoprotectant-containing sperm cell extender with substantially no sperm cell compaction particles.

7. A method for extending sorted sperm cells compromised by a sorting event as described in claim 3, wherein said step of adding a low density gradient cryoprotectant-containing sperm cell extender to said protein-containing sperm cell extender having a first protein content value comprises the step of adding a low viscosity cryoprotectant-containing sperm cell extender to said protein-containing sperm cell extender having a first protein content value.

8. A method for extending sorted sperm cells compromised by a sorting event as described in claim 1, wherein the protein-containing sperm cell extender having a first protein content value an egg-yolk-containing sperm cell extender, and wherein said step of reducing a total protein content of said protein-containing sperm cell extender to a second protein content value below said first protein content value comprises the step of reducing a total protein content of said protein-containing sperm cell extender to a percentage of egg yolk selected from the group consisting of more than about 0.4 percent egg yolk, more than about 0.8 percent egg yolk, more than about 1.6 percent egg yolk, and more than about 3.2 percent egg yolk.

9. A method for extending sorted sperm cells compromised by a sorting event as described in claim 1, further comprising the steps of:
adding a supplemental protein-containing sperm cell extender to said protein-containing sperm cell extender having a second protein content value;
increasing said total protein content of said protein-containing sperm cell extender having a second protein content value to a third protein content value higher than said first protein content value.

10. A method for extending sorted sperm cells compromised by a sorting event as described in claim 9, further comprising the step of freezing said protein-containing sperm cell extender having a third protein content value higher than said first protein content value.

11. A method for extending sorted sperm cells compromised by a sorting event as described in claim 1, wherein said step of sorting said plurality of sperm cells comprises the step of sorting said plurality of sperm cells by flow cytometery.

12. A method for extending sorted sperm cells compromised by a sorting event as described in claim 1, wherein said step of selecting said plurality of sperm cells for a desired characteristic comprises the step of selecting said plurality of sperm cells for a sex characteristic selected from the group consisting of a X-chromosome-bearing characteristic and a Y-chromosome-bearing characteristic.

13. A method for extending sorted sperm cells compromised by a sorting event as described in claim 1, wherein the protein-containing sperm cell extender having a first protein content value comprises a lipoprotein-containing sperm cell extender having a first protein content value.

14. A method for extending sorted sperm cells compromised by a sorting event as described in claim 13, wherein the lipoprotein-containing sperm cell extender having a first protein content value comprises an egg-yolk-containing sperm cell extender having a first protein content value.

15. A method for extending sorted sperm cells compromised by a sorting event as described in claim 14, where the protein-containing sperm cell extender having a first protein content value comprises a protein-containing sperm cell extender selected from the group consisting of an egg yolk based extender, a milk based extender, a citrate extender, a Tris extender, and a TEST extender.

16. A method for extending sorted sperm cells compromised by a sorting event as described in claim 1, wherein said step of adding a protein-free sperm cell extender to said protein-containing sperm cell extender having a first protein content value comprises the step of adding a protein-free cryoprotectant-containing sperm cell extender to said protein-containing sperm cell extender having a first protein content value.

17. A method for extending sorted sperm cells compromised by a sorting event as described in claim 16, wherein said step of adding a protein-free cryoprotectant-containing sperm cell extender to said protein-containing sperm cell extender having a first protein content value comprises the step of adding a glycerol-containing sperm cell extender to said protein-containing sperm cell extender having a first protein content value.

18. A method for extending sorted sperm cells compromised by a sorting event as described in claim 16, wherein said step of adding a protein-free cryoprotectant-containing sperm cell extender to said protein-containing sperm cell extender having a first protein content value comprises the step of adding a protein-free cryoprotectant-containing sperm cell extender having a volume equal to a volume of said protein-containing sperm cell extender having a first protein content value.

19. A method for extending sorted sperm cells compromised by a sorting event as described in claim 18, wherein said step of adding a protein-free cryoprotectant-containing sperm cell extender having a volume equal to a volume of said protein-containing sperm cell extender having a first protein content value comprises the step of adding a protein-free cryoprotectant-containing sperm cell extender having a volume equal to a volume of said protein-containing sperm cell extender having a first protein content value in two steps.

20. A method for extending sorted sperm cells compromised by a sorting event as described in claim 16, wherein said step of adding a protein-free cryoprotectant-containing sperm cell extender to said protein-containing sperm cell extender having a first protein content value comprises the step of adding a protein-free cryoprotectant-containing sperm cell extender to said protein-containing sperm cell extender having a first protein content value at a temperature of about 5 degrees Celsius.

21. A method for extending sorted sperm cells compromised by a sorting event as described in claim 1, wherein said step of reducing a total protein content of said protein-containing sperm cell extender to a second protein content value below said first protein content value comprises the step of reducing a total protein content of said protein-containing sperm cell extender to about 1.6 percent egg yolk.

22. A method for extending sorted sperm cells compromised by a sorting event as described in claim 1, further comprising the step of maintaining said protein-containing sperm cell extender having a second protein content value below said first protein content value in an unclarified state.

23. A method for extending sorted sperm cells compromised by a sorting event as described in claim 22, further comprising the step of subjecting said unclarified protein-containing sperm cell extender having a second protein content value below said first protein content value to centrifugation.

24. A method for extending sorted sperm cells compromised by a sorting event as described in claim 23, further comprising the step of decanting a portion of said centrifuged unclarified protein-containing sperm cell extender having a second protein content value below said first protein content value.

25. A method for extending sorted sperm cells compromised by a sorting event as described in claim 24, wherein said step of adding a supplemental protein-containing sperm cell extender to said protein-containing sperm cell extender having a second protein content value comprises the step of adding a supplemental lipoprotein-containing sperm cell extender to said protein-containing sperm cell extender having a second protein content value.

26. A method for extending sorted sperm cells compromised by a sorting event as described in claim 25, wherein said step of adding a supplemental lipoprotein-containing sperm cell extender to said protein-containing sperm cell extender having a second protein content value comprises the step of adding a supplemental egg-yolk-containing sperm cell extender to said protein-containing sperm cell extender having a second protein content value.

27. A method for extending sorted sperm cells compromised by a sorting event as described in claim 26 wherein said step of adding an egg-yolk-containing sperm cell extender to said protein-containing sperm cell extender having a second protein content value comprises the step of adding an egg-yolk-containing sperm cell extender having a percentage of egg yolk selected from the group consisting of less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, less than about 10 percent egg yolk, and less than about 5 percent egg yolk.

* * * * *